United States Patent
Smith et al.

(10) Patent No.: US 6,235,201 B1
(45) Date of Patent: May 22, 2001

(54) METHOD AND APPARATUS FOR REMOVING OIL FROM WATER INCLUDING MONITORING OF ADSORBENT SATURATION

(75) Inventors: Jeffrey J. Smith; Michael A. Berger, both of New Orleans, LA (US); Jerald W. Darlington, Jr., Marengo, IL (US); Michael R. Johnson, Mandeville, LA (US)

(73) Assignee: AMCOL International Corporation, Arlington Heights, IL (US)

( * ) Notice: Subject to any disclaimer, the term of this patent is extended or adjusted under 35 U.S.C. 154(b) by 0 days.

(21) Appl. No.: 09/352,457

(22) Filed: Jul. 13, 1999

Related U.S. Application Data (63) Continuation-in-part of application No. 09/081,976, filed on May 14, 1998, now Pat. No. 5,935,444.

(51) Int. Cl.[7] .................................................. C02F 1/40
(52) U.S. Cl. ..................... 210/691; 210/746; 210/112; 210/170
(58) Field of Search .................. 210/747, 170, 210/691, 804, 288, 266, 287, 746, 85, 502.1, 924; 166/357

(56) References Cited

U.S. PATENT DOCUMENTS

| | | | |
|---|---|---|---|
| 2,531,427 | 11/1950 | Hauser ................................. | 260/448 |
| 3,869,382 | * 3/1975 | Tajeda .................................. | 210/85 |
| 4,428,841 | 1/1984 | Favret, Jr. ............................ | 210/747 |
| 4,609,458 | * 9/1986 | Okamura et al. ..................... | 210/85 |
| 4,678,577 | 7/1987 | Thomas et al. ....................... | 210/441 |
| 4,872,991 | * 10/1989 | Bartels et al. ........................ | 210/651 |
| 5,161,619 | * 11/1992 | Bollich ................................. | 166/357 |
| 5,234,601 | * 8/1993 | Janke et al. .......................... | 210/746 |
| 5,286,383 | 2/1994 | Verret et al. .......................... | 210/521 |
| 5,474,672 | * 12/1995 | Peterson et al. ...................... | 20/85 |
| 5,567,318 | * 10/1996 | Beall .................................... | 210/691 |

FOREIGN PATENT DOCUMENTS

| | | |
|---|---|---|
| 0 787 688 A1 | 8/1997 | (EP) . |
| 5-329302 | 12/1993 | (JP) . |
| WO 82/02496 | 8/1982 | (WO) . |
| WO 83/01205 | 4/1983 | (WO) . |
| WO 88/10142 | 12/1988 | (WO) . |
| WO 95/24963 | 9/1995 | (WO) . |
| WO 99/58218 | 11/1999 | (WO) . |

OTHER PUBLICATIONS

*Mineralogy Concepts Descriptions Determinations*, Eds.—L.G. Berry and Brian Mason, W. H. Freeman and Company, San Francisco, California 1959 (pp. 508–509).

* cited by examiner

*Primary Examiner*—David A. Simmons
*Assistant Examiner*—Frank M. Lawrence
(74) *Attorney, Agent, or Firm*—Marshall, O'Toole, Gerstein, Murray & Borun (57) ABSTRACT

Apparatus in fluid communication with a water leg portion of a hydrocarbon-contaminated water, e.g., a water leg portion of an offshore drilling or production platform sump tank for conveying water, separated from oil, into contact with organophilic clay cannisters such that the hydrocarbons and other organic materials commingled with the sump tank water will be adsorbed onto the organophilic clay and detected by the embedded probe in selected cannisters. The water will pass through the clay and will be conveyed back to the ocean water without contamination. At some point in time, the organophilic clay will become "spent" and at a certain "spent level", the saturated condition of the organo-clay will be electronically detected by the embedded probe and alarm/control panel. The alarm indicates that the "spent" organophilic clay should be replaced with fresh clay or the spent clay regenerated.

37 Claims, 4 Drawing Sheets

METHOD AND APPARATUS FOR REMOVING OIL FROM WATER INCLUDING MONITORING OF ADSORBENT SATURATION

CROSS REFERENCE TO RELATED APPLICATION

This application is a continuation-in-part of application Ser. No. 09/081,976, filed May 14, 1998, now U.S. Pat. No. 5,935,444.

FIELD OF THE INVENTION

The present invention is directed to an apparatus and method for removing oil, hydrocarbons and other organic materials from water, particularly industrial waste waters, ship bilge pump waters, and rainwater collected on offshore oil drilling and production platforms, by adsorption with an oil adsorbent, while electronically monitoring the adsorbent with an embedded probe to determine when the adsorbent needs replacement. More particularly, the present invention is directed to an apparatus and method that includes relatively crude, gravity separation of oil from the water and then contacting the separated water, containing a small amount of hydrocarbons, such as oil and grease, with an organophilic clay to purify the water. During adsorption of the hydrocarbons, the adsorbent is monitored, by the probe to determine when the adsorbant is saturated and should be replaced or regenerated.

BACKGROUND OF THE INVENTION AND PRIOR ART

Offshore drilling and production platforms used for recovering oil from subterranean structure disposed beneath ocean water includes a number of structural support legs for supporting a plurality of work deck areas at substantial heights above the water level, e.g., disposed about 40 to about 100$^+$ feet above sea level. During the recovery of oil at one or more of these work deck areas, oil, grease and other hydrocarbons are unavoidably spilled onto the deck area(s) and it is not permissible to discard these hydrocarbons into the ocean water. Such work deck areas or platform surfaces are constructed to be fluid-impermeable in order to contain the spilled hydrocarbons on the work deck areas. These hydrocarbons, such as recovered oil, grease, surfactants and other organic contaminants, are directed from the work deck or platform areas, either by water washing or rain water, into a sump pump container or sump tank where the water and oil separate by gravity such that the water can be removed from a lower portion of the sump tank, for conveyance back to the ocean, and the oil can be pumped from an upper portion of the sump tank into an oil recovery container so that the oil is not returned to the ocean.

These contained deck areas on offshore structures collect a significant amount of water during periods of high rainfall. The rain water and entrained hydrocarbons, particularly recovered oil, grease and surfactants, are conveyed to the sump tank or collection tank through a gravity drain system from each of the work deck areas. These sump tanks rely on retention time as the primary oil/water separation mechanism in order to skim the lighter density hydrocarbons from a top of the sump tank so that the water can be returned to the ocean.

The sump tanks presently used on offshore platforms suffer from a number of major drawbacks which result in significant amounts of hydrocarbons, particularly oil, paraffins, grease, and refined hydrocarbons being returned to the ocean causing significant ecological contamination. One major drawback of the presently used sump tanks is that they are designed for a maximum of about three inches of rainwater per hour. It has been found that it is not uncommon to experience eight to ten inches of rainfall per hour in areas such as the Gulf of Mexico. Another major drawback of the sump tanks presently used on offshore drilling platforms is that a tank containing a layer of oil disposed above a layer of water will lose the water by evaporation over an extended dry period and the oil layer, as a result, will coat the inside surfaces of the sump tank such that water generated from even a modest rain shower, after this drying period, carries the oil through a water leg or drain portion of the sump tank as the water initially washes lower inner surfaces of the sump tank, thereby carrying the coated oil to the ocean.

In accordance with one embodiment of the present invention, there is provided an apparatus and method for treating an organic compound-containing waste water with a contained volume of an organophilic clay, the organophilic clay degrading with time due to continued adsorbance of the organic compound(s) from the waste water. The contained volume of organophilic clay includes an electrical probe disposed in contact with the organophilic clay for monitoring an electrical property of the waste water being treated, preferably monitoring the electrical conductance or electrical resistance of the waste water contacting the organophilic clay and the electrical probe, to obtain a visual or audible signal when it is time to regenerate or replace the organophilic clay (before the organophilic clay has adsorbed so much organic material that its capacity for further adsorbance of organics is insufficient to provide effluent water of sufficient purity).

In accordance with another embodiment of the present invention, the above-described drawbacks of a sump tank system for separation of water from oils and other hydrocarbons have been eliminated by the apparatus and method of the present invention wherein the sump tank water is conveyed for contact with an organophilic clay for final separation of hydrocarbons such as oil and paraffins from the water collected on work deck areas of an offshore drilling platform, while the organophilic clay is monitored so that it can be replaced before it becomes ineffective.

SUMMARY OF THE INVENTION

In brief, the present invention is directed to apparatus for monitoring adsorbance capacity of an organophilic clay by monitoring, continuously or periodically, an electrical property of the liquid being treated by the organophilic clay, particularly the electrical conductance or electrical resistance of the liquid being treated. The liquid being treated by the organophilic clay for removal of hydrocarbons therefrom can be an industrial waste water, ship bilge pump water, or, in a preferred embodiment, sump tank water collected on offshore drilling platforms (hereinafter collectively referred to as "waste water"). The organophilic clay is electronically monitored to provide a recognizable audible or visual signal, preferably an alarm, to indicate when the organophilic clay should be regenerated or replaced.

Accordingly, one aspect of the present invention is to provide a method of monitoring the changing adsorbance capacity of a contained volume of organophilic clay that is being used to treat an organic compound-containing waste water for removal of organic compounds therefrom such that a visible or audible signal is provided as an indication of when to regenerate or replace the organophilic clay.

Another aspect of the present invention is to provide a new and improved method and apparatus for complete separation of oil from water admixed on an offshore oil well drilling platform so that the separated water can be returned to the ocean without ocean contamination, with an oil adsorbent, such as an organophilic clay, while monitoring the oil adsorbent for oil saturation.

Another aspect of the present invention is to provide a new and improved method and apparatus for separation of oil and water including a first gravity separation step that provides for separation of water and oil by settling to provide layering of the water in a layer below an oil layer and then draining the lower water layer from the upper oil layer, and thereafter directing at least a portion of the separated water layer through a vessel containing an organophilic clay for contact with the organophilic clay for removal (adsorption) of remaining hydrocarbons entrained with the drained water layer, while electronically monitoring the oil adsorbent for oil saturation, such as by installing an electrical conductivity sensor within the oil adsorbent, such that a measurement of electrical conductivity of the hydrocarbon-contaminated water being treated indicates the extent of adsorption capacity remaining in the oil adsorbent.

Another aspect of the present invention is to provide a new and improved method and apparatus for separation of oil and water including a first gravity separation step that provides for separation of water and oil by settling to provide layering of the water in a layer below an oil layer and then draining the lower water layer from the upper oil layer, and thereafter directing the separated water layer through a vessel containing an organophilic clay for pressurized contact with the organophilic clay, at a pressure of about atmospheric, preferably at least 10 psig above atmospheric, for removal (adsorption) of remaining hydrocarbons entrained with the drained water layer.

The data of Table I show that at atmospheric pressure and up to less than 10 psig water pressure entering the organophilic clay-containing vessel (corresponding to the sump tank and organophilic clay-containing vessel both disposed at approximately platform level) the effluent is cloudy and contains detectable levels of oil:

TABLE I

EFFECT OF PRESSURE ON OIL ADSORPTION
BY ORGANOPHILIC CLAY

| Pressure | Influent Concentration and Color | Oil Concentration via EPA Method 413.1 | Color of Effluent |
| --- | --- | --- | --- |
| Atmospheric | 100 ppm, dark | 27 ppm | Cloudy, dark |
| 1 psig | 100 ppm, dark | 26 ppm | Cloudy, dark |
| 2 psig | 100 ppm, dark | 24 ppm | Cloudy, dark |
| 3 psig | 100 ppm, dark | 22 ppm | Cloudy, dark |
| 4 psig | 100 ppm, dark | 21 ppm | Cloudy, light |
| 5 psig | 100 ppm, dark | 20 ppm | Cloudy, light |
| 10 psig | 100 ppm, dark | 12 ppm | Clear |
| 15 psig | 100 ppm, dark | 8 ppm | Clear |
| 20 psig | 100 ppm, dark | 4 ppm | Clear |
| 25 psig | 100 ppm, dark | 1 ppm | Clear |
| 30 psig | 100 ppm, dark | 1 ppm | Clear |
| 35 psig | 100 ppm, dark | Non detect | Clear |
| 40 psig | 100 ppm, dark | Non detect | Clear |
| 45 psig | 100 ppm, dark | Non detect | Clear |
| 50 psig | 100 ppm, dark | Non detect | Clear |

The above and other aspects and advantages of the present invention will become more apparent from the following detailed description of the preferred embodiment read in conjunction with the drawings.

DETAILED DESCRIPTION OF THE PREFERRED EMBODIMENT

Figure 1:
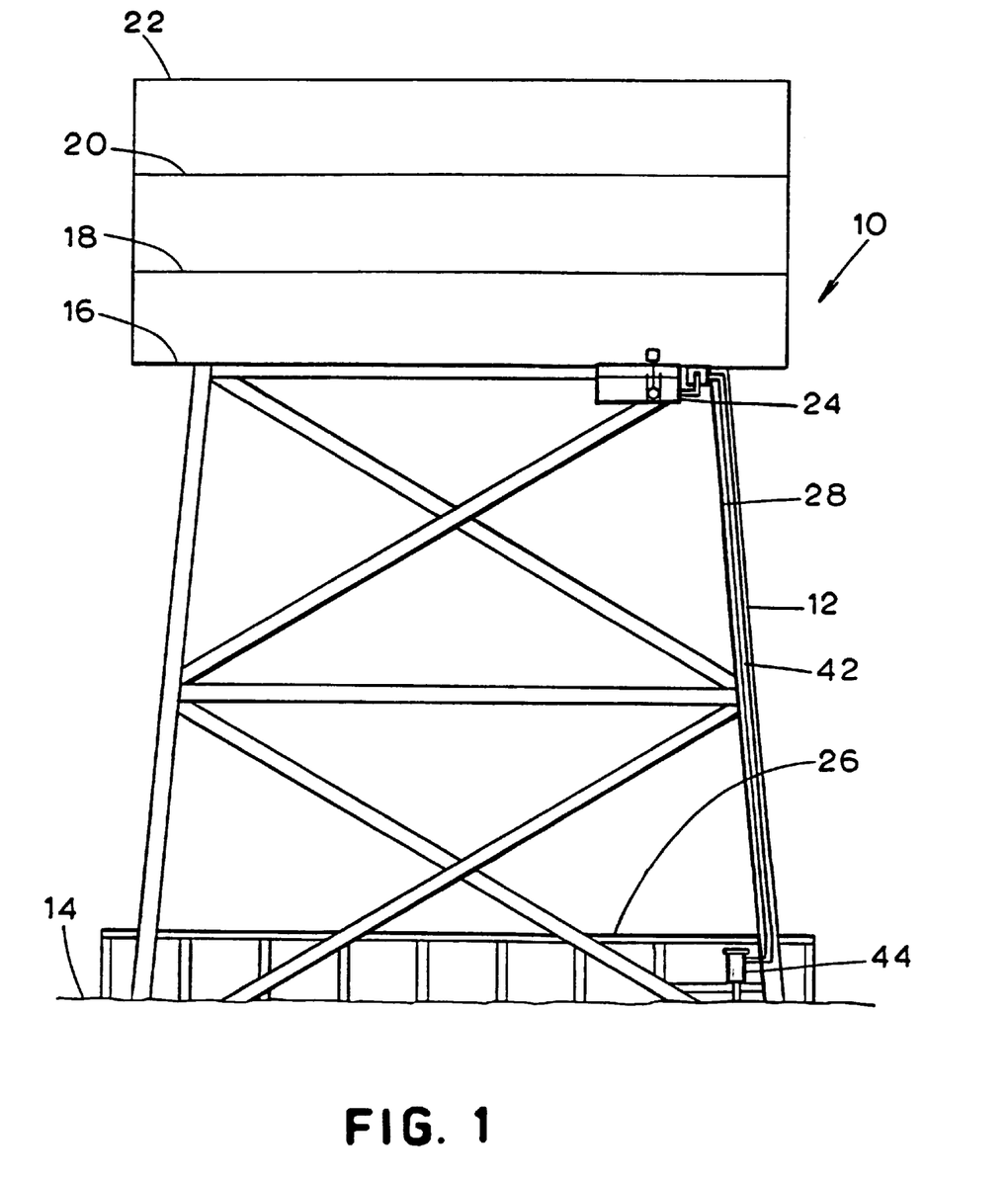
FIG. 1 is a side view of an off-shore oil well drilling platform generally showing the oil and water separating apparatus and method of the present invention attached to platform support structure.

Turning now to the drawings, and initially to FIG. 1, there is shown an offshore drilling platform generally designated by reference numeral 10, including a work deck support structure 12 for supporting a plurality of stacked work decks at a substantial height above an ocean water level 14. The work decks commonly include a cellar deck 16 at a lowest work deck level, a second deck 18 located directly above the cellar deck 16, a third deck 20 disposed directly above deck 18, and a main deck 22 at an uppermost work deck level. In extant offshore drilling platforms, a sump tank has been connected to the drilling platform 10 at the cellar deck level 16, as shown in dashed lines, and rain water, including entrained hydrocarbons, particularly oil, paraffins and surfactants have been directed from all deck levels, which are contained so that rain water and entrained hydrocarbons do not spill over to the ocean, to drain by gravity into the sump tank 24. It has been found that further separation of hydrocarbons from rain water is required for effective elimination of ocean water contamination by providing a secondary hydrocarbon recovery apparatus and method for organophilic clay treatment of the rain water separated by gravity in the sump tank 24 or 24A.

In accordance with a preferred embodiment of the present invention, it has been found that the apparatus and method of the present invention function best when the sump tank 24A is disposed on or near a boat landing deck level 26 (FIG. 1) of the offshore drilling platform 10. However, the sump tank can also be disposed at an upper level, in accordance with the present invention, as shown in dashed lines and indicated by reference numeral 24 in FIG. 1.

In accordance with a preferred embodiment of the present invention, it has been found that the apparatus and method of the present invention function best when the oil-contaminated water treated in the organophilic clay-containing vessel is pressurized above atmospheric pressure, preferably at least about 10 psig, while in contact with the organophilic clay. In accordance with an important feature of the present invention, when the contaminated water is pressurized to at least 5 psig, preferably to at least 10 psig, the effluent sent back to the ocean is clear (not cloudy) and has surprisingly less remaining oil as a result of pressurized contact of the oil-containing water with the organophilic clay.

Pressurized contact of the oil-containing water with the organophilic clay can be accomplished in a number of ways.

The preferred method of establishing pressurized contact of oil-contaminated water with the organophilic clay, when used on an offshore drilling platform, is by placement of sump tank 24A at the cellar deck level 16, and by securing the organophilic clay-containing cartridge 44 at or near the boat landing deck level 26 (such that at least a portion of the organophilic clay-containing cartridge 44 is within about 10 feet of ocean level). Oil and other hydrocarbons collected on the production decks 16, 18, 20 and 22 that may accumulate during dry weather on the inner surfaces of the conduit 28 and inner surfaces of sump tank 24 can be separated from the water that flows from the decks to the organophilic clay-containing cartridge 44 for recovery and separation in accordance with the apparatus and method of the present invention.

Figure 2:
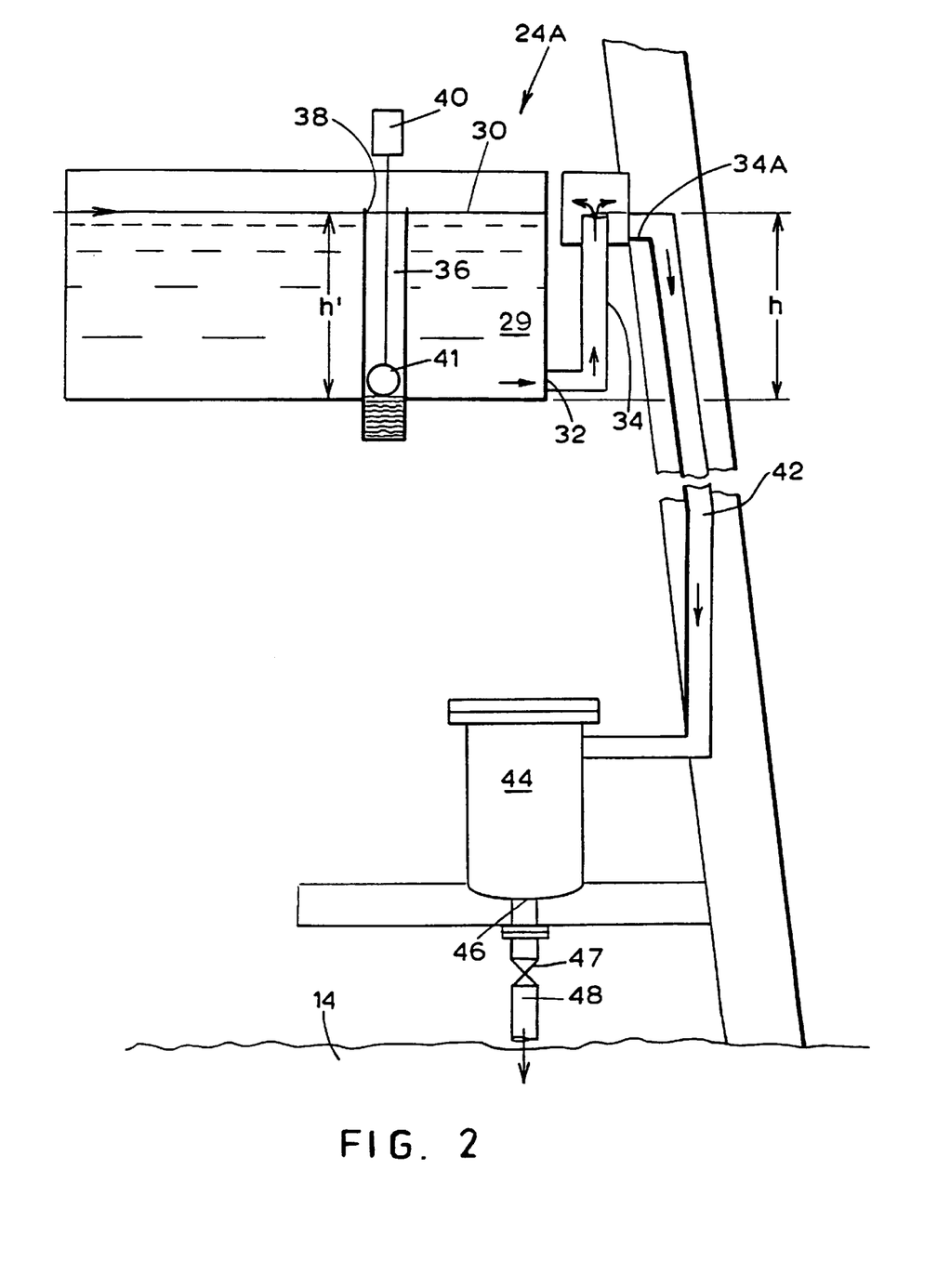
FIG. 2 is a side view of the oil and water separating apparatus and method of the present invention.
Figure 3:
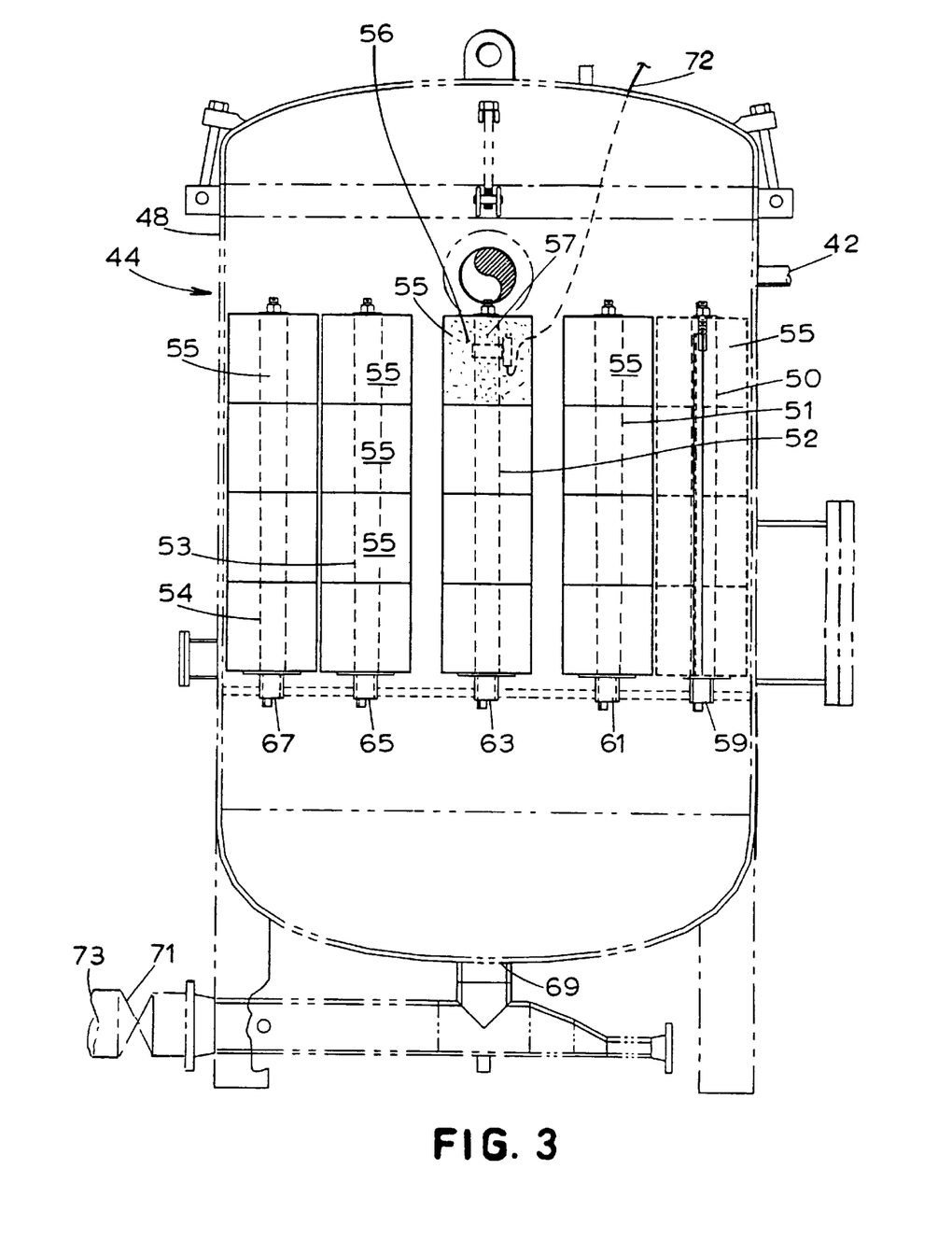
FIG. 3 is a perspective view of a preferred embodiment of an organophilic clay-containing cartridge for efficient contact of hydrocarbon-containing water with an organophilic clay contained therein.

Other expedients for establishing pressure within the organophilic clay-containing cartridge 44 include installing a valve 47 (FIG. 2), or 71 (FIG. 3) or other restrictions in the effluent conduit 48 (FIG. 2) or 73 (FIG. 3).

Water and entrained hydrocarbons are conveyed via conduit 28 from the deck areas 16, 18, 20 and 22 along the platform infrastructure or support leg 12 down to the sump tank 24 or 24A, preferably sump tank 24A, for convenient servicing and/or organophilic clay cartridge replacement. Although placement of sump tank 24A at this level has not been expedient with prior art sump tank gravity water/oil separation, it is now expedient to dispose the water/oil separation apparatus of the present invention at or near the boat landing deck level 26 (such that at least a portion of the sump tank 24A is within about 10 feet of ocean level) since oil and other hydrocarbons collected on the production decks 16, 18, 20 and 22 that may accumulate during dry weather on the inner surfaces of the conduit 28 and inner surfaces of sump tank 24A can be separated from the water that flows from the decks to the sump tank 24A for recovery and separation in accordance with the apparatus and method of the present invention.

Turning now to FIG. 2, there is shown the preferred embodiment of the hydrocarbon separation apparatus of the present invention that includes a gravity separation sump tank 24A for gravity separation of a lower level of water 29 from a floating layer of oil 30. The water 29 is conveyed through a water outlet 32 disposed near a bottom of the sump tank 24A through a water leg 34 in the shape of an inverted U. The water leg 34 achieves gravity flow of water through the water leg 34 only when the level of water within the sump tank 24A reaches height h, above an uppermost or base portion 34A of water leg 34. The sump tank 24A includes an inner, contained float valve housing 36 open at its top 38 for receiving oil from oil level 30 when the level of liquid within the sump tank 24 reaches height h'. Float valve 40 is disposed within inner housing 36 and is connected to a pump (not shown) for pumping oil into an oil recovery vessel when a floating ball portion 41 of float valve 40 rises to a predetermined level within inner valve housing 36 as a result of oil entering inner vessel 36 when the liquid level h' is reached within sump tank 24A. While h and h' are shown to be approximately equal, h may be smaller than h' in order to achieve water removal without oil pumping, as well known in the art.

In accordance with an important feature of the present invention, a downwardly extending leg portion 42 of water leg 34 is operatively interconnected to, and in fluid communication with, one or more sump water polishing units 44 containing a volume of oil adsorbent, particularly an organophilic clay. The separated water flows by gravity through water leg conduit 42 and is conveyed through conduit 42 into sump water polishing unit 44 containing organophilic clay. The organophilic clay within sump water polishing unit 44 adsorbs the hydrocarbons, oil and other organic materials entrained with the water flowing through conduits 42 and 44 for essentially complete hydrocarbon removal (less than about 10 parts per million, preferably less than about 1 part per million organics after organophilic clay treatment). The treated water flows by gravity through water exit opening 46 in the sump water polishing unit 44 and through exit conduit 48 back to the ocean water 14.

Figure 4:
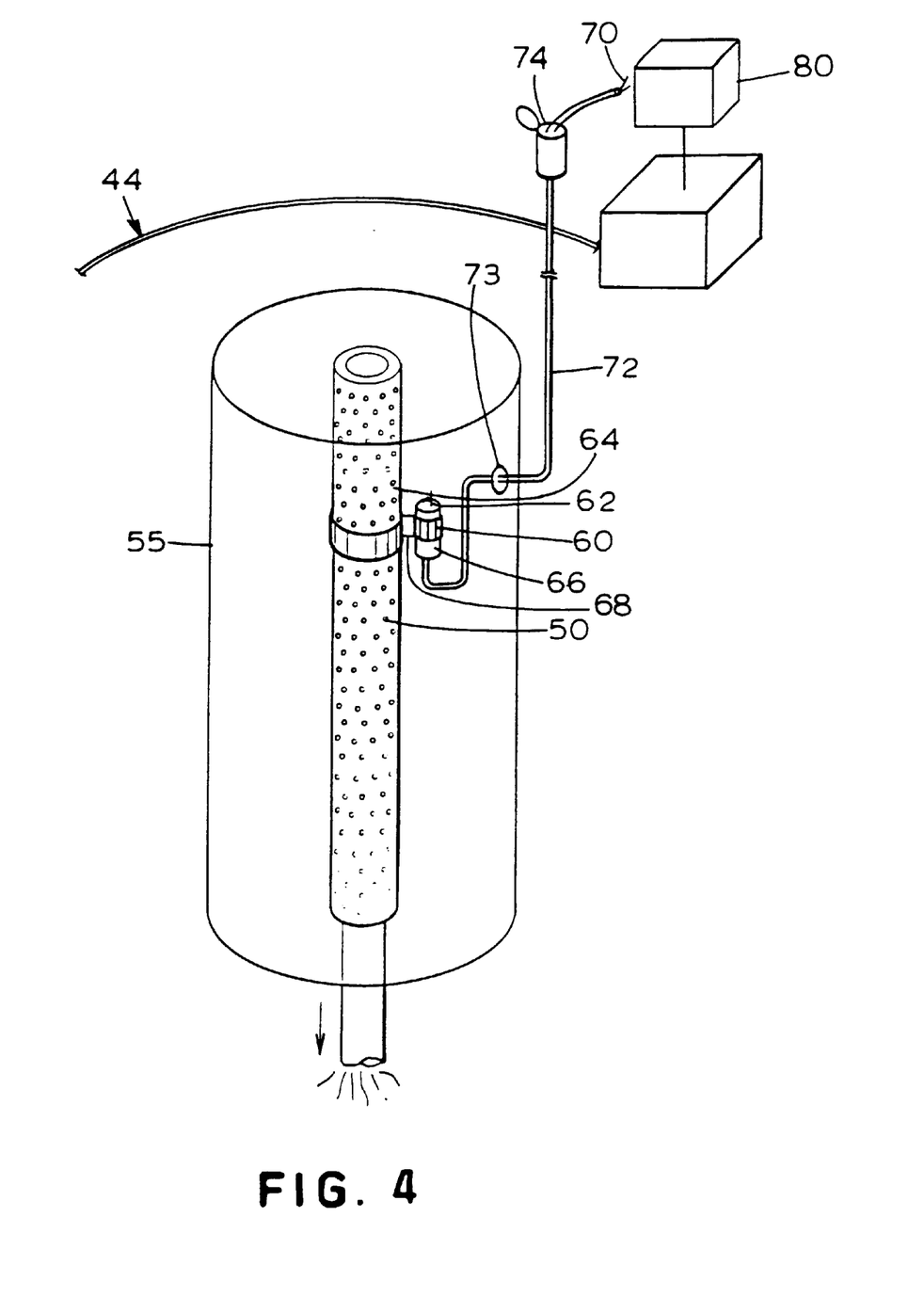
FIG. 4 is a partially broken-away side view of a preferred embodiment of a sump water polishing unit of the present invention, containing multiple, stacked cartridges (FIG. 3), so that when the cartridges of one sump water polishing unit become saturated, or nearly saturated, with hydrocarbons, the sump water can be directed into the other polishing unit while cartridges are replaced.

As shown in the preferred embodiment of FIGS. 3 and 4, the sump water polishing unit 44 includes an outer, fluid-impermeable housing 48 having a water inlet 42 interconnected through the housing 48 so that contaminated water enters the polishing unit 44 and then enters the organophilic clay-containing vessels or cartridges 55, through a plurality of apertures 56. The organophilic clay-containing cartridge 55 is water-permeable by virtue of the water flow apertures 56 that are sized sufficiently small such that organophilic clay granules do not pass therethrough. Water entering the polishing unit 44 through water inlet conduit 42 and apertures 56 flows radially inwardly into longitudinal, axial, central conduits 50, 51, 52, 53 and 54, each containing treated water-receiving apertures 57 for receiving the organophilic clay-treated water. Organophilic clay contained in cartridges 55 adsorbs any oil and organics contained in the water and the clean water exits through exit openings 59, 61, 63, 65 and 67 in each stack of cartridges 55 and the clean water collectively exits the housing 48 through exit conduit 69 and through valve 71 and then is returned to the ocean via outlet 73.

Organophilic Clay

The terms "organophilic clay" and "organoclay" are used herein interchangeably to refer to various types of clay, e.g., smectites, that have organoammonium ions substituted for cations between the clay layers. The term "organoammonium ion substituted" refers to a substituted ammonium ion in which one or more hydrogen atoms are replaced by an organic group. The organoclays are essentially solid compounds that have an inorganic and an organic phase.

The preferred clay substrates for use in this invention are the smectite-type clays, particularly the smectite-type clays that have a cation exchange capacity of at least 75 milliequivalents per 100 grams of clay. Useful clays for such purpose include the naturally occurring Wyoming variety of swelling bentonite and similar clays, and hectorite, which is a selling magnesium-lithium silicate clay. The clays are preferably converted to the sodium form if they are not already in this form. This can be effected by a cation exchange reaction with a soluble sodium compound. These methods are well-known in the art. Smectite-type clays prepared synthetically can also be utilized, such as montmorillonite, bentonite, beidelite, hectorite, saponite, and stevensite.

The organoclays useful in this invention also include those set forth in U.S. Pat. No. 2,531,427 to Hauser. These organoclays are modified clays which exhibit inorganic liquid, some of those characteristics that untreated clays exhibit in water. For example, they will swell in many organic liquids and will form stable gels and colloidal dispersions.

Generally, the quaternary ammonium salt substituted onto the clay has organic groups attached to the clay that will range from aliphatic hydrocarbon of from 1 to 24 carbons to aromatic organic molecules, such as benzyl groups that could have a host of groups substituted on the benzyl ring. The number of benzyl versus straight chain hydrocarbons substituted on the ammonium ion can vary from 3 to 0 aromatic substituents per aliphatic substituent (i.e., dimethyl dioctododecyl 0:2, methyl benzyl dioctododecyl 1:2, dibenzyl dioctobenzyl 1:1, tribenzyl octadecyl 3:1, and methyl dibenzyl octodecyl 2:1). The amount of quaternary ammonium salt substituted on the clay can vary between 0.5% to 50% by weight.

Preferred organoclays useful in the invention comprises one or more of the following types of quaternary ammonium cation-modified montmorillonite clays:

wherein $R_1$ is an alkyl group having at least 10 carbon atoms and up to, for example, 24 atoms, and preferably having a chain length of from 12 to 18 carbon atoms; $R_2$ is hydrogen, benzyl, or an alkyl group of at least 10 carbon atoms and up to, for example, 24 carbon atoms, and preferably from 12 to 18 carbon atoms; and $R_3$ and $R_4$ are each hydrogen or lower alkyl groups, i.e., they contain carbon chains of from 1 to 4 atoms, and preferably are methyl groups.

Other organoclays utilizable in the invention include benzyl organoclays such as dimethyl benzyl (hydrogenated tallow) ammonium bentonite; methyl benzyl di(hydrogenated tallow) ammonium bentonite; and more generally quaternary ammonium cation modified montmorillonite clays represented by the formula:

wherein $R_1$ is $CH_3$ or $C_6H_5CH_2$; $R_2$ is $C_6H_5CH_2$; and $R_3$ and $R_4$ are alkyl groups containing long chain alkyl radicals having 14 to 22 carbon atoms, and most preferably wherein 20% to 35% of said long chain alkyl radicals contain 16 carbon atoms and 60% to 75% of said long chain alkyl radicals contain 18 carbon atoms.

The montmorillonite clays that may be so modified are the principal constituents of bentonite rock, and have the chemical compositions and characteristics described, for example, in Berry & Mason, "Mineralogy," 1959, pp. 508–509. Modified montmorillonite clays of this type (i.e., organoclays) are commercially available from Southern Clay Products, Inc., Gonzales, Tex. under such trade designations as CLAY-TONE 34 and 40, and are available from NL Industries, Inc., New York, N.Y. under such trade designations as BEN-TONE 27, 34, and 38. Other organoclays useful in the invention are the higher dialkyl dimethyl ammonium organoclays such as dimethyl di(hydrogenated tallow) ammonium bentonite; the benzyl ammonium organoclays, such as dimethyl benzyl (hydrogenated tallow) ammonium bentonite; and ethylhydroxy ammonium organoclays such as methyl bis(2-hydroxyethyl)octodecyl ammonium bentonite.

Oil-Adsorption Monitoring Probe

The organophilic clay adsorbs oil, grease and other hydrocarbon contaminants and, after a period of time, which depends upon the flow rate and hydrocarbon contamination level of the liquid contacting the organophilic clay, the clay becomes "spent", or saturated with hydrocarbons to an extent that the clay cannot further adsorb hydrocarbons to an extent that the effluent can be legally disposed of back into the ocean. Presently, the regulations do not permit water to be returned to the ocean if it contains more than 29 ppm hydrocarbons. When the organophilic clay becomes spent, the water/oil mixture is directed from the cannister containing the spent clay and flow is contained through a cannister containing fresh or regenerated organophilic clay.

In accordance with an important feature of the present invention, it has been found that the organophilic clay within one or more cannisters 54 can be electronically monitored, continuously, or periodically, to detect when the organophilic clay is spent, or almost spent, e.g., within a short safety factor of becoming spent, so that the water flow can be directed into another cannister while regenerating or replacing the spent organophitic clay.

A waterproof probe 60 (FIG. 4), having two diametrically opposed non-corrosive conductor plates 62 and 64 extending from a probe shaft 66, is embedded in the organophilic clay within one or more of the filter cartridges 55. The probe conductor plates 62 and 64 are at a "fixed" distance from each other "d", e.g., from ½ " to 1" apart. The probe conductor plate shaft 66 preferably will be about ½ " to 1" in length and extend from a probe support structure 68. The probe support structure 68 will be affixed to a central, treated-water outlet conduit 50, 52 or 54 of the cartridge 55. Electrical wires 70 (e.g., 2 to 4) encased in a watertight jacket 72 will extend from the probe shaft 66 and penetrate through an opening in a cover 73 of cartridge 55 through an interface connector 74. A cable jacket 72 provides a waterproof seal around the electrical wires 70 and extends up from cartridge 55 through packing gland connector 74, located at the top of the cartridge 44, and wires 70 will provide for conveyance of an electrical signal from the probe 60 through the cartridge 55 that houses the organophilic clay and, in a preferred embodiment, will convey the electrical signal to a nearby control/alarm panel 80.

It is estimated that a maximum of three probes per sump water polishing unit (one per stack of cartridges 55) would be adequate to determine the adsorbed condition of the organophilic clay in the cannisters. After proper electrical connections have been accomplished, DC power is applied to the control/alarm panel 80 at a desired voltage. A calibrated signal is applied to the probes 60. When sea water or other non-hydrocarbon-contaminated reference water floods the cartridges 55, a measurement reference is established. The signal applied to the probes 60 may vary from DC to a pulsating wave in the "ultrasonic" frequency range.

As the organophilic clay begins to adsorb oil from the oily water flowing through the cannister, the sea water is displaced and squeezed away from the electrical path of the probe plates 62 and 64. The conductance/resistance reference established from non-hydrocarbon-contaminated water, e.g., sea water, flow is compared to the data measured as the oil is adsorbed by the organophilic clay. Over time, the dielectric conductance/resistance path changes—the conductance decreases and the resistance increases. The electrical path between the probe plates 62 and 64 slowly changes to a higher "dielectric" value, whereas the probe plates, dielectric and fixed distance between the plates 62 and 64 now become a "capacitor". The resulting wave shape and/or signal level produced by the capacitance and/or conductance of the media (hydrocarbon-containing sea water) is evaluated by the control/alarm panel 80. If the wave shape and/or signal level meet a predetermined criteria, the control circuitry of the panel 80 will issue an alarm signal that will be audible and/or visual and can signal any telemetry of SCADA systems.

What is claimed is:

1. A method of separating water from a combination of water and an oil contaminant comprising:

flowing said water and oil into a vessel containing an organophilic clay for intimate contact of said water and oil with said organophilic clay and adsorption of said oil contaminant on said organophilic clay while monitoring an electrical property of the water in the organophilic clay-containing vessel; and flowing the treated water out of said organophilic clay-containing vessel.

2. The method of claim 1, wherein an electrical property of the water in the organophilic clay-containing vessel is monitored by an electrical probe, including two spaced electrical conductors, disposed within the organophilic clay for measuring an electrical property of liquid disposed between said conductors, when a voltage is applied to one of said conductors, whereby a change in said electrical property of said liquid disposed between said conductors provides a measure of remaining hydrocarbon adsorbance capacity remaining in said organophilic clay.

3. The method of claim 2, further including means for providing a visual or audible signal when said remaining hydrocarbon adsorbance capacity reaches a predetermined minimum value.

4. The method of claim 1, wherein said organophilic clay-containing vessel includes an outer fluid-impermeable housing, a longitudinal, axially disposed water-sparging conduit, a fixed volume of organophilic clay surrounding a water-receiving conduit, and a water-permeable housing for containing the organophilic clay surrounding the treated water-receiving conduit, said fluid-impermeable housing including a liquid inlet and a liquid outlet.

5. The method of claim 2, wherein the spaced conductors comprise a pair of conductor plates each connected to a separate electrical conducting wire for conducting an electrical signal to a visual or audible control panel to provide a visual or audible signal from which a relative degree of remaining adsorbance capacity of hydrocarbons in the organophilic clay can be determined.

6. A method in accordance with claim 2, wherein the property of the water that is monitored is selected from the group consisting of the electrical conductance and the electrical resistance thereof.

7. The method of claim 4, wherein the pressure within the organophilic clay-containing vessel is at least 5 psig.

8. The method of claim 4, wherein the pressure within the organophilic clay-containing vessel is at least 10 psig.

9. The method of claim 4, wherein the pressure within the organophilic clay-containing vessel is in the range of 5 psig to 50 psig.

10. The method of claim 8, wherein the pressure within the organophilic clay-containing vessel is in the range of 10 psig to 50 psig.

11. A method in accordance with claim 6, wherein a signal proportional to the electrical conductance or electrical resistance of sea water is first determined as a base point in determining the change in electrical conductance or electrical resistance necessary before regeneration or replacement of the organophilic clay is effected.

12. A method of separating water from a combination of water and organics comprising:

collecting the organics and water in a settling vessel and allowing the organics and water to settle to form a lower water layer and an upper organic layer, said lower water layer including an organic contaminant;

draining a portion of the water layer from said settling vessel;

treating said drained portion of the water layer by flowing said drained portion of said water layer into a vessel containing an organophilic clay for intimate contact of said drained water with said organophilic clay and adsorption of said organic contaminant on said organophilic clay while monitoring said treated water for a change in an electrical property; and flowing the treated water out of said organophilic clay-containing vessel.

13. A method in accordance with claim 12, wherein the organophilic clay is selected from the group consisting of formula (I), formula (II), and mixtures thereof:

(I)

wherein $R_1$ is an alkyl group having at least 10 carbon atoms and up to 24 atoms; $R_2$ is hydrogen, benzyl, or an alkyl group of at least 10 carbon atoms and up to 24 carbon atoms; and $R_3$ and $R_4$ are each hydrogen or lower alkyl groups containing carbon chains of from 1 to 4 atoms;

(II)

wherein $R_1$ is $CH_3$ or $C_6H_5CH_2$; $R_2$ is $C_6H_5CH_2$; and $R_3$ and $R_4$ are alkyl groups containing long chain alkyl radicals having 14 to 22 carbon atoms.

14. A method in accordance with claim 13, wherein 20% to 35% of said $R_3$ and $R_4$ radicals contain 16 carbon atoms and 60% to 75% of said $R_3$ and $R_4$ radicals contain 18 carbon atoms.

15. A method in accordance with claim 12, wherein the property of the treated portion of the water layer that is monitored is selected from the group consisting of the electrical conductance and the electrical resistance thereof.

16. The method of claim 12, wherein the pressure within the organophilic clay-containing vessel is at least 5 psig.

17. The method of claim 13, wherein the pressure within the organophilic clay-containing vessel is at least 10 psig.

18. The method of claim 13, wherein the pressure within the organophilic clay-containing vessel is in the range of 5 psig to 50 psig.

19. The method of claim 17, wherein the pressure within the organophilic clay-containing vessel is in the range of 10 psig to 50 psig.

20. A method in accordance with claim 15, wherein a signal proportional to the electrical conductance or electrical resistance of sea water is first determined as a base point in determining the change in electrical conductance or electrical resistance necessary before regeneration or replacement of the organophilic clay is effected.

21. A method of separating water from a combination of water and oil on an offshore oil well platform disposed above an ocean, so that the oil is not returned to the ocean comprising:

collecting the oil and water in a settling vessel and allowing the oil and water to settle to form a lower water layer and an upper oil layer, said lower water layer including an oil contaminant;

draining a portion of the water layer from said settling vessel;

treating said drained portion of the water layer by flowing said drained portion of said water layer into a vessel containing an organophilic clay for intimate contact of said drained water with said organophilic clay and adsorption of said oil contaminant on said organophilic clay while monitoring an electrical property of the water treated in the organophilic clay-containing vessel; and flowing the treated water out of said organophilic clay-containing vessel and into the ocean.

22. In an offshore oil well platform for recovery of oil from beneath ocean water comprising a plurality of structural support legs, extending upwardly from the ocean, that support at least one work deck that is contained for retaining and capturing oil and rainwater thereon, said platform including oil separating means for separating said rainwater from said oil and a water conduit in fluid communication with said oil separating means for conveying separated rainwater and entrained hydrocarbons away from said separating means, the improvement comprising:

a vessel containing an organophilic clay disposed in fluid communication with said water conduit for contacting said separated rainwater and entrained hydrocarbons, conveyed away from said separating means, said vessel including a liquid outlet for flow of treated water to said ocean; and means for monitoring the degree of remaining adsorption capacity in the organophilic clay.

23. In the oil well platform of claim 22, wherein said oil separating means is secured on said platform at a location such that at least a portion of said separating means is within about 10 feet of an ocean water level.

24. In the oil well platform of claim 22, wherein said organophilic clay-containing vessel is secured to said platform support structure.

25. In the oil well platform of claim 24, wherein said organophilic clay-containing vessel is secured to said platform support structure such that at least a portion of said vessel is within 10 feet of the ocean water level.

26. In an oil well platform of claim 1, wherein said organophilic clay-containing vessel includes an outer fluid-impermeable housing including a water inlet, an axially-disposed water-permeable treated water-receiving conduit surrounded by said organophilic clay, and an embedded probe for measuring electrical conductivity of water within the organophilic clay-containing vessel, said housing including a contaminated liquid inlet and a treated liquid outlet.

27. In an oil well platform in accordance with claim 26, wherein the organophilic clay is selected from the group consisting of formula (I), formula (II), and mixtures thereof:

(I)

wherein $R_1$ is an alkyl group having at least 10 carbon atoms and up to 24 atoms; $R_2$ is hydrogen, benzyl, or an alkyl group of at least 10 carbon atoms and up to 24 carbon atoms; and $R_3$ and $R_4$ are each hydrogen or lower alkyl groups having carbon chains of from 1 to 4 atoms;

(II)

wherein $R_1$ is $CH_3$ or $C_6H_5CH_2$; $R_2$ is $C_6H_5CH_2$; and $R_3$ and $R_4$ are alkyl groups containing long chain alkyl radicals having 14 to 22 carbon atoms.

28. In the oil well platform of claim 27, wherein 20% to 35% of said $R_3$ and $R_4$ radicals contain 16 carbon atoms and 60% to 75% of said $R_3$ and $R_4$ radicals contain 18 carbon atoms.

29. In an offshore oil well platform for recovery of oil from beneath ocean water comprising a plurality of structural support legs, extending upwardly from the ocean, that support at least one work deck that is contained for retaining and capturing oil and rainwater thereon, said platform including oil separating means for separating said rainwater from said oil and a water conduit in fluid communication with said oil separating means for conveying separated rainwater and entrained hydrocarbons away from said separating means, the improvement comprising:

a vessel containing an organophilic clay disposed in fluid communication with said water conduit for contacting said separated rainwater and entrained hydrocarbons, conveyed away from said separating means, said vessel including a liquid outlet for flow of treated water to said ocean; and an electrical conductivity sensor disposed within said organophilic clay-containing vessel.

30. In the oil well platform of claim 29, wherein said oil separating means is secured on said platform at a location such that at least a portion of said separating means is within about 10 feet of an ocean water level.

31. In the oil well platform of claim 29, wherein said organophilic clay-containing vessel is secured to said platform support structure.

32. In the oil well platform of claim 31, wherein said organophilic clay-containing vessel is secured to said platform support structure such that at least a portion of said vessel is within 10 feet of the ocean water level.

33. In an oil well platform of claim 29, wherein said organophilic clay-containing vessel includes an outer fluid-impermeable housing, a longitudinal, axially disposed, central treated water-receiving conduit, a fixed volume of organophilic clay surrounding the treated water-receiving conduit, an embedded probe for electronic monitoring and a water-permeable receptacle for containing the organophilic clay disposed within the fluid-impermeable housing, said housing including a contaminated liquid inlet and a treated liquid outlet.

34. In an offshore oil well platform for recovery of oil from beneath ocean water comprising a plurality of structural support legs, extending upwardly from the ocean, that support at least one work deck that is contained for retaining and capturing oil and rainwater thereon, said platform including oil separating means for separating said rainwater from said oil and a water conduit in fluid communication with said oil separating means for conveying separated rainwater and entrained hydrocarbons away from said separating means, the improvement comprising:

a vessel containing an organophilic clay disposed in fluid communication with said water conduit for contacting said separated rainwater and entrained hydrocarbons, conveyed away from said separating means, with said organophilic clay for removing hydrocarbons entrained with said separated rainwater, said vessel including a water outlet for flow of treated water to said ocean; and an electrical probe including two spaced electrical conductors disposed within the organophilic clay for measuring an electrical property of liquid disposed between said conductors, when a voltage is applied to one of said conductors, whereby a change in said electrical property of said liquid disposed between said conductors provides a measure of remaining hydrocarbon adsorbance capacity remaining in said organophilic clay.

35. In the oil well platform of claim 34, further including means for providing a visual or audible signal when said remaining hydrocarbon adsorbance capacity reaches a predetermined minimum value.

36. In the oil well platform of claim 34, wherein said organophilic clay-containing vessel includes an outer fluid-impermeable housing, a longitudinal, axially disposed water-sparging conduit, a fixed volume of organophilic clay surrounding a treated water-receiving conduit, and a water-permeable housing for containing the organophilic clay surrounding the treated water-receiving conduit, said fluid-impermeable housing including a liquid inlet and a liquid outlet.

37. In the oil well platform of claim 34, wherein the spaced conductors comprise a pair of conductor plates each connected to a separate electrical conducting wire for conducting an electrical signal to a visual or audible control panel to provide a visual or audible signal from which a relative degree of remaining adsorbance capacity of hydrocarbons in the organophilic clay can be determined.

* * * * *